United States Patent [19]

Schaldach et al.

[11] 4,412,541

[45] Nov. 1, 1983

[54] CARDIAC PACEMAKER

[76] Inventors: Max Schaldach, Königsmarckstr. 12, 1000 Berlin 33, Fed. Rep. of Germany; J. Walter Keller, 8600 - SW. 54th Ave., Miami, Fla. 33143

[21] Appl. No.: 367,791

[22] Filed: Apr. 12, 1982

[30] Foreign Application Priority Data

Apr. 10, 1981 [DE] Fed. Rep. of Germany ....... 3115124

[51] Int. Cl.³ .............................................. A61N 1/36
[52] U.S. Cl. ............................................ 128/419 PG
[58] Field of Search ................................ 128/419 PG

[56] References Cited

U.S. PATENT DOCUMENTS

| | | |
|---|---|---|
| 3,698,398 | 10/1972 | Berkovits . |
| 3,903,897 | 9/1975 | Woolons et al. ............. 128/419 PG |
| 3,937,226 | 2/1976 | Funke . |
| 3,939,844 | 2/1976 | Pequignot . |
| 3,947,534 | 3/1976 | Allen et al. .................. 128/419 PG |
| 4,049,004 | 9/1977 | Walters ......................... 128/419 PG |
| 4,088,140 | 5/1978 | Rockland et al. ............ 128/419 PG |
| 4,091,817 | 5/1978 | Thaler . |
| 4,114,628 | 9/1978 | Rizk . |
| 4,163,451 | 8/1979 | Lesnick et al. . |
| 4,181,133 | 1/1980 | Kolenik et al. ............. 128/419 PG |
| 4,248,238 | 2/1981 | Joseph ......................... 128/419 PG |
| 4,250,883 | 2/1981 | Thompson . |
| 4,273,133 | 6/1981 | Hartlaub et al. . |
| 4,328,807 | 5/1982 | Jirak et al. ................... 128/419 PG |

FOREIGN PATENT DOCUMENTS

| | | |
|---|---|---|
| 2455237 | 7/1975 | Fed. Rep. of Germany . |
| 2528817 | 1/1976 | Fed. Rep. of Germany . |
| 2739490 | 3/1978 | Fed. Rep. of Germany . |
| 2701104 | 7/1978 | Fed. Rep. of Germany ...... 128/419 PG |
| 2701481 | 7/1978 | Fed. Rep. of Germany . |
| 2845323 | 5/1979 | Fed. Rep. of Germany . |
| 2943583 | 5/1980 | Fed. Rep. of Germany . |
| 2944572 | 5/1980 | Fed. Rep. of Germany . |
| 2944596 | 5/1980 | Fed. Rep. of Germany . |
| 2944631 | 5/1980 | Fed. Rep. of Germany . |

*Primary Examiner*—William E. Kamm
*Attorney, Agent, or Firm*—Spencer & Kaye

[57] ABSTRACT

A cardiac pacemaker constructed for terminating tachyarrhythmias and including: an atrial electrode implantable in a patient's heart for supplying atrial stimulation pulses thereto and at which a pulse appears in response to each atrial contraction; a ventricular electrode implantable in the patient's heart for supplying ventricular stimulation pulses thereto, and at which a pulse appears in response to each ventricular contraction; separately switchable control paths connected to each electrode for causing one electrode to produce a stimulation pulse at a given time after the occurrence of a pulse on the other electrode; a first time delay unit connected to be actuated by signals derived from the heart behavior for supplying a stimulating pulse to the ventricular electrode at a time after the occurrence of a pulse on the atrial electrode, which is shorter than the physiological atrial-ventricular transfer time; and a second time delay unit connected to be actuated by signals derived from the heart behavior for supplying a stimulating pulse to the atrial electrode at a time after the occurrence of a pulse on the ventricular electrode which is shorter than a selected physiological period in the operation of the heart.

15 Claims, 14 Drawing Figures

CARDIAC PACEMAKER

BACKGROUND OF THE INVENTION

The present invention relates to cardiac pacemakers.

Cardiac stimulation is presently a clinically and therapeutically accepted method for correcting various degrees of heart block and specific other arrhythmias. One recently developed technique, sometimes termed "physiological stimulation", involves stimulation of not just the ventricles or just the atria, but both sets of chambers. Studies have been conducted of the so-called sequential stimulation over a wide range of stimulation parameters in connection with a study of the hemodynamic properties of the heart, as reported in an article by Samet et al, entitled "Hemodynamic Sequelae of Atrial, Ventricular and Sequential Atrial Ventricular Pacing in Cardiac Patients", *American Heart Journal*, Volume 72, pages 725–729, December, 1966.

Earlier than that, p-wave synchronous coupling of the stimulation of both chambers was found to produce substantially better antiarrhythmia properties than stimulation of the ventricle exclusively. As described by Nathan et al in an article entitled "An Implantable Synchronous Pacemaker for the Long Term Correction of Complete Heart Block", *American Journal of Cardiology*, Volume 11, page 362, 1963. Bradycardia have been treated with a corresponding ventricular rhythm which completed with, or was out of synchronism with, the true sinus rate.

Implantable versions of AV-sequential pacemakers, as they are disclosed in U.S. Pat. No. 3,747,604 and which are based on the work reported in the above-cited article by Samet et al, provided atrial escape stimuli before ventricular escape stimuli so that the protection against arrhythmias is augmented particularly in the bradycardial area. In this connection, the term "escape stimuli" is intended to mean that the artificial cardiac pacemaker emits a stimulation pulse unless a corresponding signal appears from the heart itself within a given interval.

Studies and observations with arrhythmias described by Castellanos et al in the article entitled "Preliminary Studies with an Implantable Multimode A-V Pacemaker for Reciprocating Atrioventricular Tachycardias". PACE, Volume 3, No. 3, May, 1980, indicate ways in which arrhythmias can be initiated, eliminated and suppressed by suitable stimulation of one of the two chambers of the heart, even if in some patients coupling is effected in the reverse direction.

The literature on cardiac arrhythmias is replete with diagrams and listings of criteria for the "reentry-arrhythmias" of the dominant type where two stimulation pathways must exist to maintain the arrhythmia. It is also shown there that the delay period of the loop must be relatively long to meet the requirement for sustained reentry. All prior art attempts to terminate tachyarrhythmias by stimulation have the drawback that the success quota in the various methods per se is not yet satisfactory.

SUMMARY OF THE INVENTION

It is an object of the present invention to provide a cardiac pacemaker of the above-described type which offers improved possibilities for terminating such reentry arrhythmias.

The above and other objects according to the invention are achieved by the provision of a cardiac pacemaker constructed for terminating tachyarrhythmias and including an atrial electrode implantable in a patient's heart for supplying atrial stimulation pulses thereto and at which a pulse appears in response to each atrial contraction, and a ventricular electrode implantable in the patient's heart for supplying ventricular stimulation pulses thereto, and at which a pulse appears in response to each ventricular contraction, which pacemaker further includes: separately switchable control paths connected to each electrode for causing one electrode to produce a stimulation pulse at a given time after the occurrence of a pulse on the other electrode; a first time delay unit connected to be actuated by signals derived from the heart behavior for supplying a stimulating pulse to the ventricular electrode at a time after the occurrence of a pulse on the atrial electrode, which is shorter than the physiological atrial-ventricular transfer time; and a second time delay unit connected to be actuated by signals derived from the heart behavior for supplying a stimulating pulse to the atrial electrode at a time after the occurrence of a pulse on the ventricular electrode which is shorter than a selected physiological period in the operation of the heart.

The invention is based to a substantial extent on the realization that a plurality of control pathways, or patterns, must be available to master the normal and abnormal physiological delays which cause the heart to beat at undesirably fast rates.

Prior to the present invention, none of the intensive efforts in connection with prosthetic stimulation treatments recognized the fact that it is necessary to control the sequence or pathway of cardiac activation in both directions within a single stimulation concept.

Although it has been found that in some patients shorter AV delays are of advantage to terminate an arrhythmia state, in other patients a retrograde stimulation of the atria produced more favorable results. The idea of using both pathways simultaneously in a single unit has not been examined in the prior art, although one of the prerequisites for such arrhythmia, which has been known for a long time, is the existence of two paths of which at least one has a relatively long transit delay.

A significant advantage of the present invention is that the manner of providing an artificial parallel path in one direction aids to suppress tachycardias in some patients and additional means increase the number of arrhythmia patients responding to stimulation therapy. The total number of patients whose needs can thus be met is greater than could be expected merely by the sum of those for whom each of the two measures is appropriate since the two therapeutic measures supplement one another and are able to produce termination of a tachyarrhythmia even in those cases where one of the two measures alone would not have accomplished this.

The criteria stated in the cited prior art show a relationship of the propagation time through natural and additional paths to the stimulation interval and a relationship of the refractory period to the stimulation interval. These relative values are important factors here which initiate or enhance the beginning or continuation of the tachycardia.

It is evident from the cited literature that the propagation time may also be extended in proportion to the tissue refractory period if the stimulation cycles are shortened. If early tissue stimulation somewhere along the loop proves to be refractory in one direction and, once it continues on the other path, proceeds through the loop at a relatively slow rate, it will not find all of the tissue to be refractory upon further propagation. This is the basic mechanism of reentry arrhythmia. The reentry into the loop can be interrupted by increasing the refractory period or by reducing the propagation delay somewhere in the loop. In this connection, it is a significant further desirable property of the additional parallel path according to the invention that the respective periods are shortened with the cycle interval, or are at least not lengthened, so as to compensate in this way the above-mentioned physiological changes.

Another advantage of the cardiac pacemaker according to the invention is that the recognition and selection for stimulation of those parts of the cardiac cycle which can be influenced by pacing makes it possible to achieve a relatively great resistance to interference with respect to signal events not emanating from the heart.

BRIEF DESCRIPTION OF THE DRAWINGS

FIGS. 3b through 3g are time diagrams showing the pulse behavior of various groups of pacemaker components with respect to the EKG signals shown in FIG. 3a.

DESCRIPTION OF THE PREFERRED EMBODIMENTS

Figure 1:
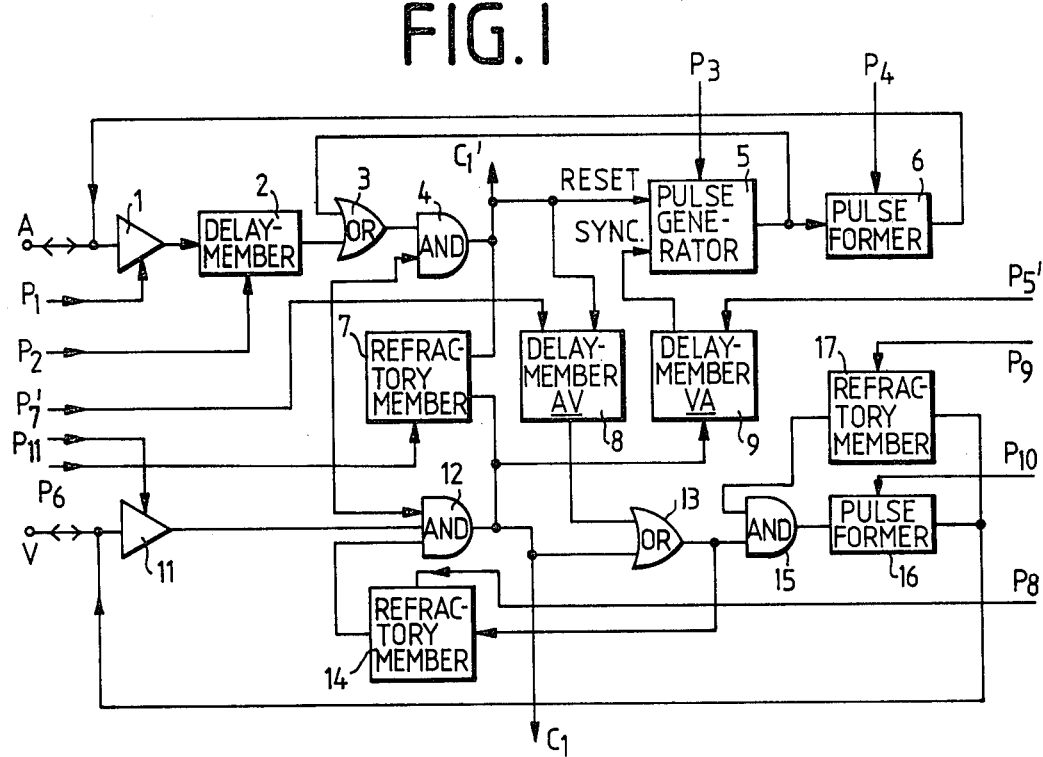
FIG. 1 is a block circuit diagram of those elements of a pacemaker according to a preferred embodiment of the invention which serve to generate stimulation pulses and to receive and process intracardial signals.

In the circuit shown in FIG. 1, the terminal A is connected to an electrode placed in a cardiac atrium. The signal detected by the atrial electrode travels to a preamplifier 1 in which the signal is increased in amplitude until it is sufficient for actuating the subsequent stages. For the following description, it has been assumed that positive logic is employed and that an electrical H (high) state corresponds to the presence of signals or pulses.

The preamplifier 1 is followed by a delay member 2 which produces a signal delay of a few milliseconds. The output of the delay member 2 is followed by an OR gate 3 whose output leads to one of the inputs of an AND gate 4. The output of the AND gate 4 is connected with the RESET input of a pulse generator 5. Generator 5 operates to generate an output pulse at the end of a given period of time following the preceding reset, unless it has been reset via its RESET input before the end of that period, and pulse emission is thus inhibited. The output signal of the pulse generator 5 controls a pulse former circuit 6 in which, upon appearance of an output pulse from generator 5, there is generated a stimulation pulse signal for the atria which travels to the terminal A to which is connected the electrode leading to an atrium.

The pulse generator 5 further includes a sync input connected to receive a sync input pulse which synchronizes the pulse generator, i.e. causes the immediate emission of an output pulse. Even if there is such an output pulse which was actuated by the sync input signal, the pulse generator 5 will be reset by the signal conducted from its output to the further input of the OR gate 3 unless the AND gate 4 is blocked due to the fact that its further input is at an electrical L (low or ground) potential.

This blocking of the AND gate 4 is effective also for pulses coming from the output of the delay member 2 to the OR gate 3 and is initiated by a sensing A-refractory delay member 7 which emits at its output a logic H signal for a defined period of time after a pulse has reached one of its inputs. In a possible embodiment of the present invention, this refractory member 7 includes a retriggerable monoflop and thus blocks the AND gate 4 for a period of time after a signal from the atria or from the ventricles has been detected via further circuitry to be described below.

The above-described components constitute an atrial demand pacemaker in which atrial pulses become independently active after a given maximum period of time and artificial stimulation pulses are emitted when a given natural heart frequency is not reached. For a given period of time after the emission of an artificial stimulation pulse or the detection of a signal from the heart itself, the pacemaker becomes refractory.

Within the concept of a programmable pacemaker, the amplification factor of the input amplifier 1 can be programmed by signals applied via a line $P_1$, the delay period of the delay member 2 can be programmed through a line $P_2$, the natural frequency of the pulse generator 5 upon the absence of RESET pulses can be programmed through a line $P_3$ and the amplitude of the output pulses of the amplifier 6 can be programmed through a line $P_4$.

A further part of the pacemaker is formed by an input amplifier 11 for receiving ventricle signals. This amplifier is connected with the terminal V for an electrode disposed in a ventricle and its output is connected to one input of an AND gate 12 whose output signals reach an OR gate 13. The output signal from the OR gate 13 controls a sensing V-refractory delay member 14, which, for a given period of time beginning with a pulse emitted by the OR gate 13, emits an L signal which is applied to a further input of the AND gate 12 to block this gate and thus prevent passage of a signal received from the ventricle by the preamplifier 11 during the above-mentioned given period of time. A corresponding block is also effected by an L signal traveling from the output of the refractory member 7 to a further input of the AND gate 12, so that the conductive path for ventricle signals can be inhibited in two different ways for periods of time of different lengths. The refractory member 7 is then also activated by signals emanating from the input of the atrium preamplifier 1.

The refractory member 14 blocks the actuation of ventricle stimulation pulses whenever a signal is emitted by the OR gate 13, i.e. when signals are received at terminal V with AND gate 12 not blocked, for a period of 400 ms.

The output signal of the OR member 13, in principle, reaches an AND gate 15 which controls an output stage 16 having the form of a pulse former stage for generating the ventricle stimulating signals. The output of stage 16 is connected with the terminal for the ventricle electrode V and thus simultaneously with the input amplifier 11.

An additional refractory delay member 17 is actuated by pulses generated by the output stage 16. In response to these pulses, this refractory member 17 emits an L signal for a given period of time so as to block the AND gate 15 with respect to further signal pulses appearing from OR gate 13.

The refractory member 17 here forms a time member for the ventricular output signal. It serves to limit the rate of ventricular stimulation. If due to interference the sinus rate has a tendency to actuate too short a pulse train in the pacemaker the blocking time of member 17, preferably 400 ms, constitutes a rate limitation providing safety for the patient.

The signal path for amplifying the signals derived from the ventricle or for generating stimulation pulses for the ventricle usually includes means which, by themselves, when triggered by heart activity located in the ventricle, generate stimulation pulses for the ventricle unless the period following between pulses is so short that one of the refractory members 7, 14 or 17 prevents, via AND gate 12 or 15, respectively, the transfer of the pulses to the subsequent circuit member. Thus, as a response to a signal detected in the atrium or in the ventricle, the refractory member 7 blocks the further processing of pulses in both signal paths. This does not inhibit pulse generator 5 in the processing path for the atrium signals so that it still produces an output signal at the end of its reset period, while in the signal path for signals detected in the ventricle the generation of stimulation pulses which may possibly fall into the vulnerable phase of the heart is prevented.

In the normal case, a VA delay member 9 emits a signal with a delay by 25 ms after a pulse reaches its input from AND gate 12, i.e. after a signal is emitted by input amplifier 11 when the AND gate 12 is not being blocked by the refractory member 7 or 14. Based on the selected refractory periods, such a signal pulse would originate from a premature ventricular contraction.

The output signal of the delay member 9 reaches the sync input of the pulse generator 5 and thus causes immediate emission of a pulse by the pulse output stage 6 of the atrial signal path so that the pulse generator 5 is reset as well. The output signal of AND gate 4 simultaneously goes to the refractory member 7 which causes the emission by member 7 of a pulse determining the atrial refractory period. The delay period of the delay member 9 has been selected to be very short so that the subsequent stimulation pulse for the atrium is emitted almost immediately thereafter.

A further delay member 8, whose delay period during normal operation corresponds to the physiological AV transfer period of about 170 ms is connected with the output of the AND gate 4 and emits, upon the presence of a pulse at the gate 4 output, a delayed output signal. The pulse at the output of gate 4 also resets the pulse generator 5, i.e. is processed as a pulse appearing outside the refractory period. The output signal of the delay member 8 reaches a further input of the OR gate 13 which, passing via AND gate 15, actuates the output stage 16 and thus actuates a stimulation pulse for the ventricle.

The delay members 8 and 9 can be varied with respect to their delay periods by programming signals applied via lines $P_{7'}$ and $P_{5'}$, respectively, by programming means to be described below.

The refractory member 17 can be influenced by means of a further programming line $P_9$; the input amplifier 11, the refractory member 14, and the amplitude of the pulses emitted by the output stage 16 can be influenced by signals applied via means of programming lines $P_{11}$, $P_8$ and $P_{10}$, respectively.

The operation of the above described pacemaker portion will now be described with reference to FIGS. 3a through 3g.

Figure 3A:
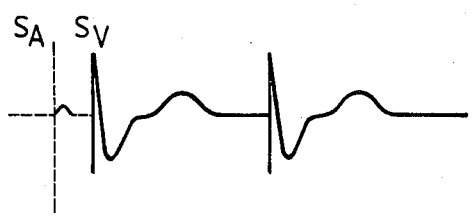
FIG. 3a is a signal diagram of EKG signals used to explain the operation of the invention.
Figure 3B:
Figure 3C:
Figure 3D:
Figure 3E:
Figure 3F:
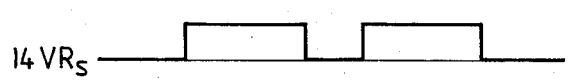
Figure 3G:
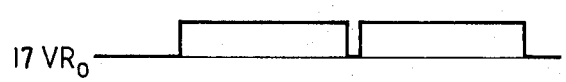

FIG. 3a shows the curve of an EKG signal; in FIGS. 3a to 3c, the pulses $S_A$ represent stimulation pulses in the atria and pulses $S_V$ represent stimulation pulses in the ventricles. The signal patterns shown in FIGS. 3b and 3c are the outputs from stages 6 and 16, respectively. FIG. 3d shows a signal AV constituting the output from member 8 and containing pulses whose duration corresponds to the atrial-ventricular transfer period. Pulses corresponding to the atrial refractory period and the output from member 7 are shown in FIG. 3e, while FIGS. 3f and 3g depict the outputs of members 14 and 17, respectively, having pulses whose durations correspond to the ventricle refractory periods $VR_s$ and $VR_o$, respectively. It can be seen that the total refractory period for the input signals (sensing for the ventricle is composed of the sum of the AV delay and the refractory period $VR_s$ of member 14.

The refractory periods—as they are shown in FIGS. 3d through 3g—depending from pulses appearing in ventricle or atrium decisively determine the possibilities of the pacemaker becoming acitve by way of stimulation in the sense of terminating tachyarrhythmias. The pulses shown in broken lines in FIG. 3 are not necessarily present and depend on the operating state of the pacemaker or on prior cardiac behavior. For example, pulse $S_A$ in FIG. 3a will appear only if no spontaneous pulse appears within the time window given by the refractory period.

The following comments are additionally significant in connection with the operation of the above-described pacemaker.

Since the ventricle pulse generator is never inhibited unless a partial block exists, there is no requirement in the illustrated embodiment for interference suppression means. Furthermore, there exists a significant difference between the atrial and ventricular pulse output functions. The atrial system generates pulses which are independent of the escape type. The ventricle pulse is dependent either on the atrial, ventricular or interference events and never occurs spontaneously.

Since the simultaneous detection of a ventricular systole may occur at both electrodes of a unipolar conductor system attached to the heart, the delay member 2 generates a brief delay of a few milliseconds to assure that this signal is evaluated correctly and is not interpreted as an event in the atrium. With the delay in member 2, a normal P wave blocks and actuates a new cycle with a slight delay. If the first event in this cycle is a premature ventricle contraction, the short delay in the atrial processing permits the ventricular input circuit to continue and to control the behavior.

In prior art sequential systems this delay was not necessary since there was no need to distinguish premature events in unidirectional systems.

After passing through the AND gate 4, the atrial signal actuates an atrial refractory period represented by the pulse produced by refractory member 7. Independent of whether the atrial event occurred spontaneously or as a result of stimulation, the refractory member 7 takes care, by way of its refractory function, that the atrial as well as the ventricular signal reception for gates 4 and 12, respectively, is blocked.

It must further be noted that the atrial pulse generator 5 is able to react in two different ways. In the case of an atrially sensed heartbeat, the pulse generator is set to a starting state in the manner of an oscillator which generates a signal when no pulse appears. The oscillator 5 is reset to the starting point of the cycle and at the end of the cycle a stimulus is generated. As for a ventricularly recorded event, the atrial pulse generator 5 is set ahead in time via its sync terminal so that the oscillator is synchronized with the end of the cycle and emits an atrial stimulus before a new cycle is actuated.

The AV delay member 8 forms a programmable time interval between a ventricularly determined event and the stimulus produced by retrograde transfer.

In the normal case, when the atrial systole appears first and the atrial as well as the ventricular signal detection is blocked, the AV delay member 8 constituting a clock pulse generator is started and at the end of the generated signal pulse a trigger signal is generated as the ventricular output pulse, in output stage 16, after the pulse has passed through the OR gate 13 and the AND gate 15.

Figure 2:
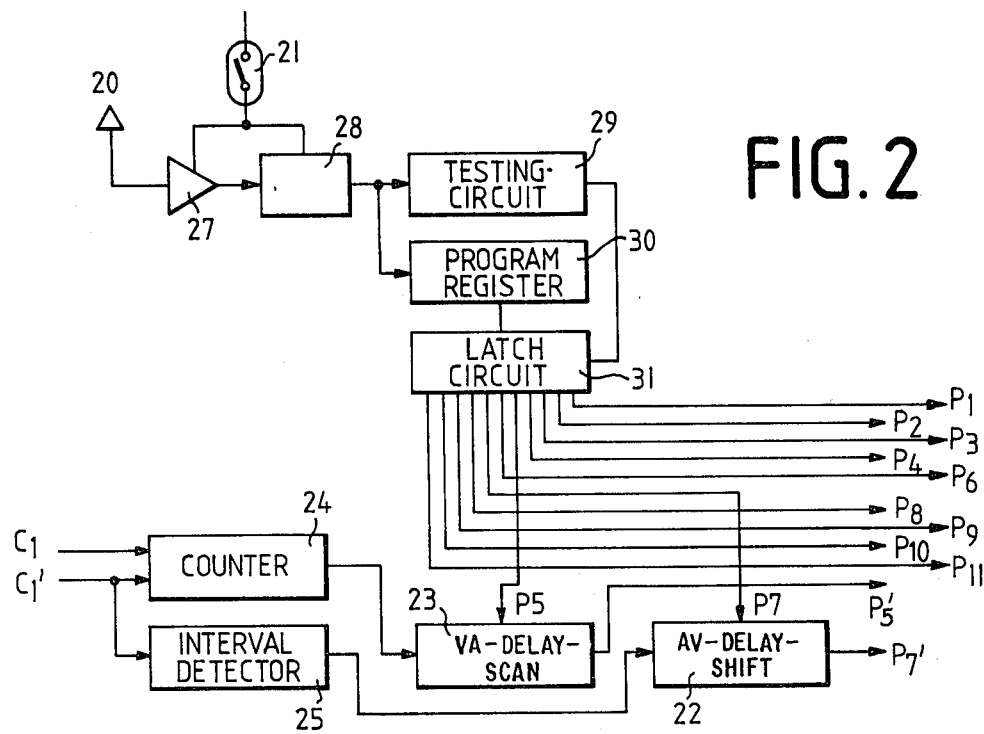
FIG. 2 is a block circuit diagram of programming means for the circuit of FIG. 1 and of additional circuit means required according to the invention.

FIG. 2 shows, in the form of a block circuit diagram, additional components which supplement the function of the pacemaker components shown in FIG. 1. Included in this are, on the one hand, means which permit, in the sense of programming, influencing of various parameters of the pacemaker as listed above. A signal received by an antenna 20 provided in the pacemaker and containing the operating values for the pacemaker in coded form is transmitted, if a reed switch 21 is also closed by means of a magnet, via an input amplifier 27 to a detector 28 which reads the received values, after checking in a testing circuit 29 for plausibility or the like, into a program register 30, the individual operating values for the pacemaker being placed on appropriate conductors in accordance with the program via a latch, or distributor, circuit 31.

The program signals for the VA delay control $P_5$, and for the AV delay control $P_7$, are influenced, in accordance with the invention, by further circuit means which operate in dependence on the heart signals. A signal detected from the ventricle electrode and appearing at the output of the AND gate 12, and which does not fall into any of the refractory periods for ventricular signals, i.e. constitutes an extrasystole, goes from the output $C_1$ in FIG. 1 to the corresponding input of the circuit in FIG. 2 and thus advances a counter 24 for premature ventricle signals which in turn advances the VA-delay-scan circuit 23 containing a control value for the VA delay, starting from a minimum value of 25 ms. by one step of 12.2 ms with each count until the delay reaches a maximum value of 87.5 ms. This step-wise advancing is also effected by every further corresponding signal from the ventricle and thus converts the control signal for the VA delay appearing on line $P_5$, as set by the external programming means, into an output signal $P_5$, which reaches the delay member 9 of FIG. 1 and causes the timing of the VA delay member 9 to be set effectively.

The counter 24 is reset by a reset signal supplied via line $C_1$, whenever a pulse appears at the output of the AND gate 4, i.e. a signal is detected in the atrium outside of the atrium refractory period. The signal on $C_1$, simultaneously actuates an interval detector 25 which emits an output signal whenever the time between two atrium signals falls below the given time interval of 380 ms. However, according to another preferred embodiment of the invention (not shown) these means may also respond accordingly, whenever the average sinus rate within a given time period exceeds a limit value. The output signal from the interval detector 25 activates a switching device 22 for the AV delay which reduces the delay determined by signal $P_7$, and produces modified output signal $P_7$,. This reduction is cancelled whenever the sinus rate returns to a normal value or the interval between two atrium pulses from the heart itself has reached its normal value again.

The AV delay of the delay member 8 can thus be programmed or set not only from the pacemaker program memory but its value also is automatically shortened, via the timing circuit of block 25 in FIG. 2 (from 170 to 85 ms), if sinus intervals result which fall below a given value. The shortened intervals for the AV delay can be influenced from outside the body just as those of the VA delay, via the above-mentioned programming means.

Correspondingly, the VA delay period of the delay member 9 can be set via the program in memory 30 of FIG. 2 and is automatically increased via the control circuit 23 with every subsequent ventricular pacemaking event. The counter 24 of FIG. 2 is reset to zero by a signal on line $C_1$, originating form AND gate 4 in FIG. 1 and appears, after a first pulse originating from the atrium has appeared, either spontaneously or as a demand pulse.

If the ventricular output signal is blocked by a signal corresponding to a premature contraction in the ventricle (PVC), it is desirable, according to the present invention, that this PVC signal be detected and processed, i.e. an atrial stimulus be generated to block every additional path in the heart and to reset the physiological timer to begin a new heart cycle and to assure that the next transferred heartbeat does not fall into the vulnerable phase of a premature ventricular heartbeat.

Figure 4:
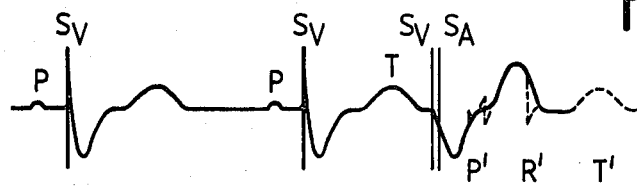
FIGS. 4 through 8 are diagrams illustrating the emission of stimulation pulses for atria and ventricles in dependence on various intracardial signals recorded via the input stages of the pacemaker.

FIG. 4 shows this process for an exemplary EKG curve. FIG. 4 is a heartbeat waveform diagram depicting two normal, pacer-assisted sinus beats followed by a ventricle pulse $S_V$ and an atrial pulse $S_A$ provoked by a PVC. The pulse $S_A$ resets the sinus, or heartbeat, cycle, pre-empting conduction of an accessory path that could produce heartbeat waves P', R' and T'. This represents a primary distinguishing function of a bidirectional pacer. In the illustrated case, the provoked $S_A$ and $S_V$ pulses are essentially simultaneous.

It will now be explained how the signals, or pulses, must be processed which are determined very early by the ventricular input system. Obviously, any signal occurring before the ventricular recovery time cannot be of ventricular origin and should remain without influence on the pacemaker. Such interfering signals, e.g. electrode artifacts, chemical depolarization after the stimulus, the T wave or electromagnetic interference, are suppressed by the refractory period of the ventricle input circuit. Care is taken, moreover, that atrial stimulus signals or spontaneous atrial activities assure the programmed ventricular stimulus in any case, the recording of ventricular signals being superfluous in that period of time which begins with the P wave of the EKG and ends shortly before the T wave. The ventricular refractory period thus extends from the beginning of either an atrial or ventricular event to the end of the refractory period $VR_s$.

For the person skilled in the art it is obvious that all these parameters should be modifiable without surgical invasion. The parameter values which are controlled by the program memory register 30 of the system (FIG. 2) are given in their respective values. Amplifier 27 effects amplification of the signal carrier, which carrier may be HF, magnetic, optical, etc. The detector 28 forms a receiver for the signal for changing or setting the program in register 30. The detector is locked by the latch 31 which monitors the fulfillment of the criteria of the code determined by the testing circuit 29.

In the description below, several modes of operation will be explained which are typical for the pacemaker according to the invention.

Figure 5:
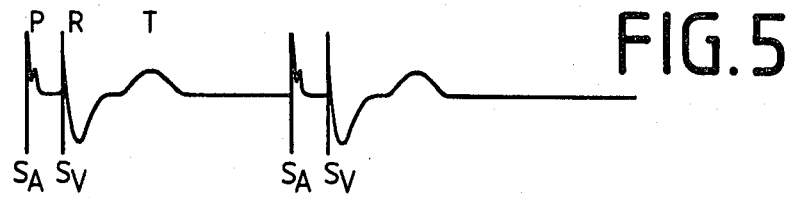

1. On the assumption that the sinus rate has a value of only 30 beats/min (sinus Bradycardia), the pacemaker generates, as shown in FIG. 5, an atrial stimulus $S_A$ followed by a ventricular stimulus $S_V$ with a given escape rate and a given time delay between each $S_A$ pulse and its associated $S_V$ pulse.

Figure 6:
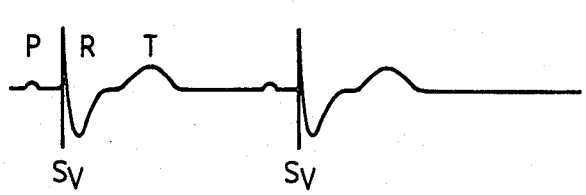

2. Referring to FIG. 6, if this sinus rate is greater than the escape rate of the pacemaker (for example 85 heartbeats per minute) the pacemaker sets back the atrial pulse generator without emitting an atrial stimulus ($S_A$). A ventricular stimulus $S_V$ is generated at the end of the given time interval independently of any requirement. A prerequisite here is a one-to-one transfer and a relatively normal cardiac activity with or without physiological transfer.

Figure 7:
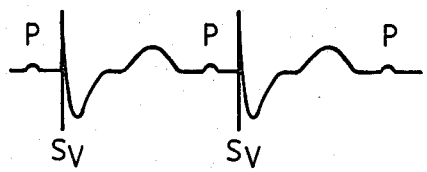

3. If the sinus rate exceeds a given value of, for example, 95 heartbeats per minute, the pacemaker generates ventricular pulses $S_V$ which appear in synchronism with the atrial signal from the heart itself but at a given shortened AV delay interval, as shown in FIG. 7. This shortening of the AV delay occurs automatically together with a nonrefractory, premature atrial contraction.

Figure 8:
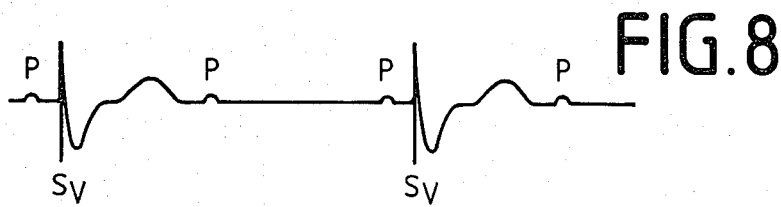

4. On the assumption that the sinus rate is higher than a given maximum value for the heart rate of, for example, 160 heartbeats per minute, a ventricular pulse $S_V$ is emitted in synchronism, simultaneously or almost simultaneously in time, with a pulse in the atrium. The shortened AV delay results in a transfer, at a ratio of one for every two beats, to the ventricle which then has a rate of 80 heartbeats, as shown in FIG. 8. Medically this is considered to be a second degree block.

5. If, as before, the contraction is not prematurely refractory, but occurs merely before the next atrial escape time, the pacemaker emits ventricular as well as atrial pulses with a given VA delay, this delay period being increased with repeated occurrence and the first cycle originating from the sine node causes the system to be set back to the starting state. This sequence is shown in FIG. 4.

The premature ventricular contraction thus actuates an immediate atrial stimulus. If the next heartbeat originates properly from the atrium, the scanning function is interrupted and made inactive until again two or more heartbeats have occurred without sinus control. Scanning is continued until there is natural sinus activity or obvious sinus activity or until a given count is reached in counter 24 of FIG. 2.

The design of the above-mentioned component groups corresponds to that of prior art pacemakers for digitally operating circuits with discrete or programmed logic circuits, the individual, analog operating circuits (input amplifiers, output pulse formers) also corresponding, per se, to prior art circuits.

It will be understood that the above description of the present invention is susceptible to various modifications, changes and adaptations, and the same are intended to be comprehended within the meaning and range of equivalents of the appended claims.

What is claimed is:

1. A cardiac pacemaker constructed for terminating tachyarrhythmias and including an atrial electrode implantable in a patient's heart for supplying atrial stimulation pulses thereto and at which a pulse appears in response to each atrial contraction, and a ventricular electrode implantable in the patient's heart for supplying ventricular stimulation pulses thereto, and at which a pulse appears in response to each ventricular contraction, said pacemaker further comprising: separately switchable means connected to each said to electrode for causing one said electrode to produce a stimulation pulse at a given time after the occurrence of a pulse on the other said electrode; first time delay means connected to be actuated by signals derived from the heart behavior for supplying a stimulating pulse to said ventricular electrode at a time after the occurrence of a pulse on said atrial electrode, which is shorter than the physiological atrial-ventricular transfer time; and second time delay means connected to be actuated by signals derived from the heart behavior for supplying a stimulating pulse to said atrial electrode at a time after the occurrence of a pulse on said ventricular electrode which is shorter than a selected physiological period in the operation of the heart.

2. Pacemaker as defined in claim 1 wherein said first time delay means is connected to be actuated by signals caused by an increased heartbeat rate or premature heartbeat.

3. Pacemaker as defined in claim 2 further comprising a detector connected to said first time delay means for setting the timing thereof in accordance with the interval between successive atrial contractions.

4. Pacemaker as defined in claim 1 wherein said second delay means are connected to be actuated by pulses on said ventricular electrode.

5. Pacemaker as defined in claim 4 further comprising means connected to said second time delay means for increasing the delay produced thereby from an initial short value in steps each produced by a respective actuation signal supplied to said second delay means.

6. Pacemaker as defined in claim 5 wherein said means connected to said second time delay means comprise a counter connected to count the actuation signal supplied to said second time delay means.

7. Pacemaker as defined in claim 6 wherein said counter is connected to be reset to its starting state by each signal actuating said first time delay means.

8. Pacemaker as defined in claim 1 further comprising at least one refractory delay member connected for preventing the supply of stimulation pulses at one said electrode for a first selected time after appearance of a pulse on one of said electrodes.

9. Pacemaker as defined in claim 8 wherein said refractory delay member comprises means for superimposing a delay representing the atrial refractory period on a delay representing the ventricular refractory period so that the ventricular refractory period is extended by an additional delay corresponding to the normal delay between an atrial and a ventricular contraction.

10. Pacemaker as defined in claim 8 wherein said refractory delay member is connected to prevent the supply of stimulation pulses to one said electrode for the selected time after appearance of a pulse on the same electrode.

11. Pacemaker as defined in claim 1 wherein said separately switchable means comprise a timed pulse generator connected to said atrial electrode for supplying a stimulation pulse thereto at the end of a selected period of time during which no pulse appears on said atrial electrode.

12. Pacemaker as defined in claim 1 wherein said switchable means are constructed to respond to essentially simultaneous pulses at both said atrial and ventricular electrodes by assigning priority to the ventricular electrode pulse and to process such pulses as if originating at said ventricular electrode.

13. Pacemaker as defined in claim 12 wherein said switchable means comprise a delay member connected to impart a predetermined time delay to pulses appearing at said atrial electrode.

14. Pacemaker as defined in claim 1 further comprising programming means for adjusting the operating parameters of said pacemaker and for setting time delays therein to values applicable to normal operation.

15. Pacemaker as defined in claim 14 wherein said programming means are arranged for adjusting those parameters which become effective only upon activation of said time delay means.

* * * * *